United States Patent
Patel et al.

(10) Patent No.: US 10,519,493 B2
(45) Date of Patent: Dec. 31, 2019

(54) APPARATUS AND METHOD FOR IMAGE ANALYSIS OF A FLUID SAMPLE UNDERGOING A POLYMERASE CHAIN REACTION (PCR)

(71) Applicant: FluxErgy, LLC, Irvine, CA (US)

(72) Inventors: Tej Rushikesh Patel, Aliso Viejo, CA (US); Ryan Alan Revilla, Downey, CA (US); Roy James Heltsley, Foothill Ranch, CA (US)

(73) Assignee: Fluxergy, LLC, Irvine, CA (US)

( * ) Notice: Subject to any disclaimer, the term of this patent is extended or adjusted under 35 U.S.C. 154(b) by 593 days.

(21) Appl. No.: 15/185,714

(22) Filed: Jun. 17, 2016

(65) Prior Publication Data

US 2016/0369324 A1 Dec. 22, 2016

Related U.S. Application Data

(60) Provisional application No. 62/182,992, filed on Jun. 22, 2015, provisional application No. 62/187,471, filed on Jul. 1, 2015.

(51) Int. Cl.
| | |
|---|---|
| *C12Q 1/686* | (2018.01) |
| *C12Q 1/689* | (2018.01) |
| *C12Q 1/70* | (2006.01) |
| *G01N 21/64* | (2006.01) |
| *G06K 9/20* | (2006.01) |
| *G06T 7/00* | (2017.01) |
| *B01L 7/00* | (2006.01) |

(52) U.S. Cl.
CPC ............. *C12Q 1/686* (2013.01); *C12Q 1/689* (2013.01); *C12Q 1/701* (2013.01); *G01N 21/6428* (2013.01); *G06K 9/2081* (2013.01); *G06T 7/0012* (2013.01); *G06T 7/0016* (2013.01); *B01L 7/52* (2013.01); *B01L 2300/0654* (2013.01); *B01L 2300/18* (2013.01); *G01N 21/6456* (2013.01); *G01N 2021/6439* (2013.01); *G06T 2207/10016* (2013.01); *G06T 2207/10024* (2013.01); *G06T 2207/10064* (2013.01); *G06T 2207/20021* (2013.01); *G06T 2207/30072* (2013.01)

(58) Field of Classification Search
None
See application file for complete search history.

(56) References Cited

U.S. PATENT DOCUMENTS

| | | | |
|---|---|---|---|
| 5,229,297 A | 7/1993 | Schnipelsky et al. | |
| 5,976,336 A | 11/1999 | Dubrow et al. | |
| 6,068,752 A | 5/2000 | Dubrow et al. | |
| 6,071,478 A | 6/2000 | Chow | |
| 6,153,073 A | 11/2000 | Dubrow et al. | |
| 6,235,175 B1 | 5/2001 | Dubrow et al. | |
| 6,303,343 B1 | 10/2001 | Kopf-Sill | |
| 6,399,025 B1 | 6/2002 | Chow | |
| 6,428,987 B2 | 8/2002 | Franzen | |
| 6,437,551 B1 | 8/2002 | Krulevitch et al. | |
| 6,576,459 B2 | 6/2003 | Miles et al. | |
| 7,033,474 B1 | 4/2006 | Dubrow et al. | |
| 7,309,467 B2 | 12/2007 | Chen et al. | |
| 7,431,888 B2 | 10/2008 | Frechet et al. | |
| 7,678,336 B2 | 3/2010 | Chang et al. | |
| 7,811,523 B2 | 10/2010 | Bjornson | |
| 7,867,754 B1 | 1/2011 | Regnier et al. | |
| 7,883,669 B2 | 2/2011 | Sun et al. | |
| 7,915,030 B2 | 3/2011 | Inoue et al. | |
| 7,919,062 B2 | 4/2011 | Yuen | |
| 7,981,237 B2 | 7/2011 | Park et al. | |
| 8,053,239 B2 | 11/2011 | Wheeler et al. | |
| 8,158,926 B2 | 4/2012 | Feng et al. | |
| 8,202,491 B2 | 6/2012 | Masters et al. | |
| 8,216,827 B2 | 7/2012 | Pouteau et al. | |
| 8,247,176 B2 | 8/2012 | Pourahmadi et al. | |
| 8,289,519 B2 | 10/2012 | Zare et al. | |
| 8,343,778 B2 | 1/2013 | Li et al. | |

(Continued)

FOREIGN PATENT DOCUMENTS

| | | |
|---|---|---|
| WO | 1993022054 | 11/1993 |
| WO | 2014055963 | 4/2014 |

OTHER PUBLICATIONS

Cady, Nathaniel C., et al. "Real-time PCR detection of Listeria monocytogenes using an integrated microfluidics platform." Sensors and Actuators B: Chemical 107.1 (2005): 332-341.*
Jarvius, Jonas, et al. "Digital quantification using amplified single-molecule detection." Nature methods 3.9 (2006): 725.*
Lui, Clarissa, Nathaniel Cady, and Carl Batt. "Nucleic acid-based detection of bacterial pathogens using integrated microfluidic platform systems." Sensors 9.5 (2009): 3713-3744.*
Boehm, Douglas A., Philip A. Gottlieb, and Susan Z. Hua. "On-chip microfluidic biosensor for bacterial detection and identification." Sensors and Actuators B: Chemical 126.2 (2007): 508-514.*

(Continued)

*Primary Examiner* — G Steven Vanni
(74) *Attorney, Agent, or Firm* — K&L Gates LLP

(57) ABSTRACT

Apparatuses and for causing a point-of-care polymerase chain reaction and analyzing the polymerase chain reaction at the point-of-care, particularly when unwanted bubbles are present during the polymerase chain reaction, are described herein. In a general embodiment, a device for analyzing a polymerase chain reaction in a fluid sample includes a current source configured to cause the polymerase chain reaction by heating the fluid sample within a target zone, a camera imaging device configured to record a plurality of images of the fluid sample in the target zone while the current source causes the polymerase chain reaction, and a controller configured to (i) distinguish wanted objects in the plurality of images from an unwanted object in the plurality of images, and (ii) determine whether the fluid sample tests positive or negative for a bacteria or virus based on the wanted objects.

22 Claims, 13 Drawing Sheets

(56) References Cited

U.S. PATENT DOCUMENTS

| | | |
|---|---|---|
| 8,349,276 B2 | 1/2013 | Pamula et al. |
| 8,367,021 B2 | 2/2013 | Kennedy et al. |
| 8,394,341 B2 | 3/2013 | Reinhardt et al. |
| 8,409,848 B2 | 4/2013 | Zeng et al. |
| 8,540,946 B2 | 9/2013 | Padmanabhan et al. |
| 8,557,199 B2 | 10/2013 | Heath et al. |
| 8,557,518 B2 | 10/2013 | Jovanovich et al. |
| 8,562,918 B2 | 10/2013 | Jovanovich et al. |
| 8,592,157 B2 | 11/2013 | Pourahmadi et al. |
| 8,597,574 B2 | 12/2013 | Gumbrecht et al. |
| 8,603,414 B2 | 12/2013 | Omuro et al. |
| 8,790,595 B2 | 7/2014 | Polwart et al. |
| 8,852,527 B2 | 10/2014 | Thomas et al. |
| 8,874,273 B2 | 10/2014 | Sun et al. |
| 8,894,946 B2 | 11/2014 | Nielsen et al. |
| 8,911,636 B2 | 12/2014 | Gautham |
| 8,911,989 B2 | 12/2014 | Lee et al. |
| 8,936,762 B2 | 1/2015 | Ehrlich et al. |
| 8,940,147 B1 | 1/2015 | Bartsch et al. |
| 8,962,252 B2 | 2/2015 | Liang et al. |
| 9,017,946 B2 | 4/2015 | Hasson |
| 9,114,398 B2 | 8/2015 | Knight et al. |
| 9,138,744 B2 | 9/2015 | Tsao et al. |
| 9,170,138 B2 | 10/2015 | Giovangrandi et al. |
| 9,328,344 B2 | 5/2016 | Link et al. |
| 9,335,247 B2 | 5/2016 | Sharpe et al. |
| 9,364,833 B2 | 6/2016 | Bergstedt |
| 9,540,686 B2 | 1/2017 | Zeng et al. |
| 2003/0155344 A1 | 8/2003 | Cobb |
| 2004/0193202 A1 | 9/2004 | Allen |
| 2005/0196779 A1 | 9/2005 | Ho et al. |
| 2005/0233440 A1 | 10/2005 | Scurati et al. |
| 2006/0094028 A1 | 5/2006 | Danna et al. |
| 2007/0015179 A1 | 1/2007 | Klapperich |
| 2007/0154895 A1 | 7/2007 | Spaid et al. |
| 2007/0163175 A1 | 7/2007 | Kihara et al. |
| 2007/0190828 A1 | 8/2007 | Goldman et al. |
| 2008/0241910 A1 | 10/2008 | Jung et al. |
| 2008/0253633 A1 | 10/2008 | Xia et al. |
| 2009/0053726 A1 | 2/2009 | Owen et al. |
| 2009/0140170 A1 | 6/2009 | Nevill et al. |
| 2009/0143233 A1 | 6/2009 | Knight et al. |
| 2009/0186404 A1 | 7/2009 | Kim et al. |
| 2009/0215157 A1 | 8/2009 | Jung et al. |
| 2009/0215194 A1 | 8/2009 | Magni et al. |
| 2009/0311717 A1 | 12/2009 | De Sonneville et al. |
| 2010/0203521 A1 | 8/2010 | Klapperich et al. |
| 2010/0291584 A1 | 11/2010 | Tseng et al. |
| 2011/0039280 A1 | 2/2011 | Leary et al. |
| 2011/0206545 A1 | 8/2011 | Junod et al. |
| 2011/0269131 A1 | 11/2011 | Chiu et al. |
| 2011/0301535 A1 | 12/2011 | Takayama et al. |
| 2011/0315559 A1 | 12/2011 | Holt et al. |
| 2012/0140055 A1 | 6/2012 | Narusawa et al. |
| 2012/0145253 A1 | 6/2012 | Zeng et al. |
| 2012/0195810 A1 | 8/2012 | Cohen et al. |
| 2012/0244043 A1 | 9/2012 | LeBlanc et al. |
| 2012/0244604 A1 | 9/2012 | Kornilovich |
| 2012/0283108 A1 | 11/2012 | Sambas |
| 2012/0309010 A1 | 12/2012 | Shuber |
| 2013/0052725 A1 | 2/2013 | Yazdanfar |
| 2013/0149215 A1 | 6/2013 | Dekker et al. |
| 2013/0224781 A1 | 8/2013 | Jung et al. |
| 2013/0236907 A1 | 9/2013 | Petersen et al. |
| 2013/0244906 A1 | 9/2013 | Collins |
| 2013/0345096 A1 | 12/2013 | Wan |
| 2014/0038191 A1 | 2/2014 | Liang et al. |
| 2014/0141424 A1 | 5/2014 | Pourahmadi et al. |
| 2014/0161686 A1 | 6/2014 | Bort et al. |
| 2014/0199764 A1 | 7/2014 | Domansky et al. |
| 2014/0200154 A1 | 7/2014 | Sugarman et al. |
| 2014/0248621 A1 | 9/2014 | Collins |
| 2014/0295441 A1 | 10/2014 | Egan et al. |
| 2014/0307931 A1 | 10/2014 | Gierahn et al. |
| 2014/0309508 A1 | 10/2014 | Kim et al. |
| 2015/0024426 A1 | 1/2015 | De Oliveira Garcia Da Fonseca et al. |
| 2015/0125947 A1 | 5/2015 | Korczyk et al. |
| 2015/0238967 A1 | 8/2015 | Erickson et al. |
| 2015/0290644 A1 | 10/2015 | Prentice et al. |
| 2016/0033311 A1 | 2/2016 | Giovangrandi et al. |
| 2016/0069913 A1 | 3/2016 | Bakhru et al. |
| 2016/0144358 A1 | 5/2016 | Patel |
| 2016/0296933 A1 | 10/2016 | Chiou et al. |
| 2016/0334351 A1 | 11/2016 | Lu et al. |
| 2016/0340716 A1 | 11/2016 | Ortac et al. |
| 2017/0001196 A1 | 1/2017 | Zhang et al. |
| 2017/0008009 A1 | 1/2017 | Azpiroz et al. |
| 2017/0021354 A1 | 1/2017 | Kim et al. |
| 2017/0058324 A1 | 3/2017 | Balog et al. |

OTHER PUBLICATIONS

Liu, Hao-Bing, et al. "Micro air bubble formation and its control during polymerase chain reaction (PCR) in polydimethylsiloxane (PDMS) nnicroreactors." Journal of Micromechanics and Microengineering 17.10 (2007): 2055.*

International Preliminary Report on Patentability issued in related International Patent Application No. PCT/US2016/038152 dated Jun. 28, 2017.

Miralles et al., "A Review of Heating Temperature Control in Microfluidic Systems: Techniques and Applications," Diagnostics, 2013, No. 3, pp. 33-67.

Wang et al., "A miniaturized quantitative polymerase chain reaction system for DNA amplification and detection." Sensors and Actuators, No. B 141, 2009, pp. 329-337.

Hsieh et al., "Enhancement of thermal uniformity for a microthermal cycler and its applicaiton for polymerase chain reaction," Sensors and Actuators, B 130 (2008), pp. 848-856.

International Preliminary Report on Patentability issued in related International Patent Application No. PCT/US2016/038124 dated Jun. 26, 2017.

International Preliminary Report on Patentability issued in related International Patent Application No. PCT/US2016/038157 dated Jun. 19, 2017.

International Search Report and Written Opinion issued in related International Patent Application No. PCT/US2016/038152 dated Sep. 14, 2016. 12 pages.

International Search Report and Written Opinion issued in related International Patent Application No. PCT/US2016/038124 dated Sep. 8, 2016. 12 pages.

International Search Report and Written Opinion issued in related International Patent Application No. PCT/US2016/038157 dated Oct. 28, 2016. 12 pages.

* cited by examiner

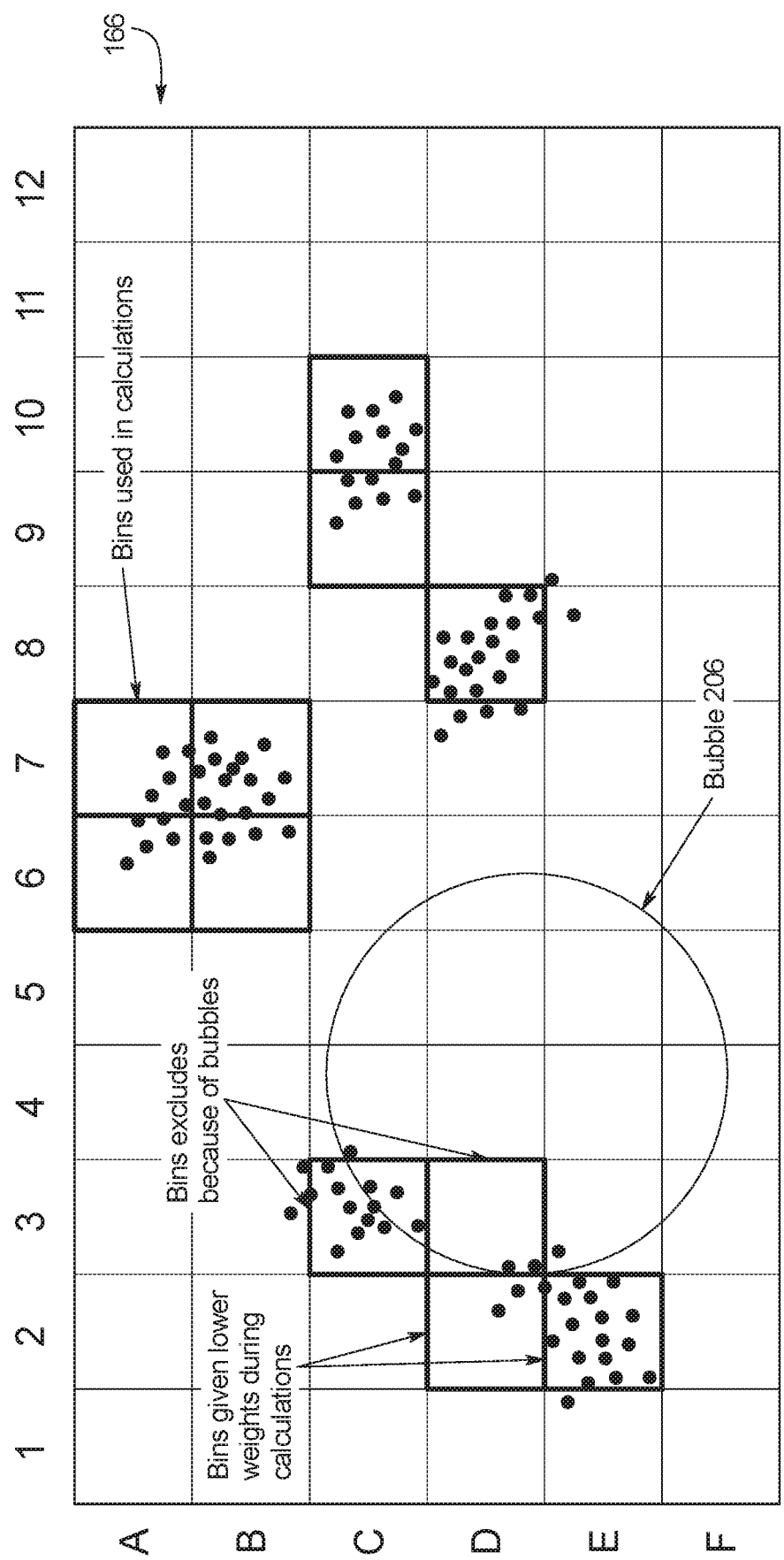

APPARATUS AND METHOD FOR IMAGE ANALYSIS OF A FLUID SAMPLE UNDERGOING A POLYMERASE CHAIN REACTION (PCR)

PRIORITY CLAIM AND CROSS-REFERENCE TO RELATED APPLICATIONS

This application claims priority to U.S. Provisional Patent Application No. 62/182,992, entitled "Point-Of-Care PCR Assay for Infectious Agents", filed Jun. 22, 2015, and U.S. Provisional Patent Application No. 62/187,471, entitled "Point-Of-Care PCR Assay for Infectious Agents", filed Jul. 1, 2015; the entire contents of each of which are hereby incorporated by reference and relied upon. This application is also related to U.S. application Ser. No. 15/185,640, entitled "Device for Analyzing a Fluid Sample and Use of Test Card with Same", filed concurrently herewith, and U.S. application Ser. No. 15/185,661, now U.S. Pat. No. 10,214,772, entitled "Test Card for Assay and Method of Manufacturing Same", filed concurrently herewith, the entire contents of each of which are hereby incorporated by reference and relied upon.

FIELD OF THE DISCLOSURE

The present disclosure relates generally to apparatuses and methods for performing an assay, and more specifically to apparatuses and methods for causing a point-of-care polymerase chain reaction and analyzing the polymerase chain reaction at the point-of-care.

BACKGROUND OF THE DISCLOSURE

Point-of-care (POC) in vitro diagnostics tests (IVDT) have traditionally had two major categories, nucleic acid amplification tests (NAAT) or immunoassay-based tests. The former directly detects the pathogen's DNA or RNA, while the latter detects antibodies or antigens generated by the immune system response to the pathogen.

Current POC diagnostic immunoassays lack the high sensitivity and specificity of nucleic acid amplification methods. This becomes more pronounced during the initial stages of infection, often within 168 hours. Taking the case of Dengue virus in whole blood, immunoglobulin M (IgM) and immunoglobulin G (IgG) remain undetectable in the majority of patients until 5 and 10 days post-infection, respectively, whereas nucleic acid can be found as early as 0 to 7 days. Moreover, many immunoassay tests are unable to detect infectious agents until 3 months after the initial onset of the infection. This delay is due to the time it takes for the body's immune system to respond to an infection.

POC diagnostic assays developed utilizing NAATs have very high sensitivities and specificities, matching those of currently accepted laboratory tests. The primary mechanism of NAAT based systems is to directly detect an infectious agent's nucleic acid, lending to the test's ability to detect diseases within the first few days of the onset of infection. In addition, by careful primer design, NAATs also have the ability to have very high specificity and sensitivity compared to immunoassay based testing. The largest drawback of NAATs compared to immunoassay-based tests is the complicated equipment and/or processes required to prepare a sample for testing.

SUMMARY OF THE DISCLOSURE

Described herein are methods and apparatus for causing a point-of-care polymerase chain reaction and analyzing the polymerase chain reaction at the point-of-care, particularly when unwanted bubbles are present during the polymerase chain reaction. In a general embodiment, a device for analyzing a polymerase chain reaction in a fluid sample includes a current source configured to cause the polymerase chain reaction by heating the fluid sample within a target zone, a camera imaging device configured to record a plurality of images of the fluid sample in the target zone while the current source causes the polymerase chain reaction, and a controller configured to (i) distinguish wanted objects in the plurality of images from an unwanted object in the plurality of images, and (ii) determine whether the fluid sample tests positive or negative for a bacteria or virus based on the wanted objects.

In an example embodiment, the wanted objects are nucleic acid molecules and the unwanted object is an air bubble.

In an example embodiment, the controller is configured to analyze the plurality of images by dividing the target zone into a plurality of bins.

In an example embodiment, the plurality of bins are arranged in a grid with a plurality of rows and columns.

In an example embodiment, the controller is configured to determine whether the fluid sample has tested positive or negative for the bacteria or virus by selecting at least two of the plurality of bins that overlap a cluster of wanted objects and calculating a mean fluorescence value of the at least two of the plurality of bins.

In an example embodiment, the controller is configured to exclude at least one of the plurality of bins from the mean fluorescence value calculation if the at least one of the plurality of bins overlaps the unwanted object.

In an example embodiment, the controller is configured to assign a weight to at least one of the plurality of bins used in the mean fluorescence value calculation based on the proximity of the at least one of the plurality of bins to the unwanted object.

In an example embodiment, the controller is configured to exclude at least one of the plurality of bins if the at least one of the plurality of bins does not meet a minimum threshold value for brightness.

In an example embodiment, the controller is configured to report an inconclusive test if the controller identifies an unwanted image in the plurality of images.

In an example embodiment, the device includes a user interface, the controller includes a plurality of preprogrammed analyses that can be performed on the fluid sample, and the user interface is configured to allow a user to select at least one analysis from the plurality of preprogrammed analyses.

In an example embodiment, the plurality of images includes at least one of: (i) a plurality of still images of the polymerase chain reaction recorded by the camera imaging device over a period of time; or (ii) a video image of the polymerase chain reaction recorded by the camera imaging device over the period of time.

In an example embodiment, the controller is configured to distinguish the wanted objects in the plurality of images from the unwanted object in the plurality of images by comparing a size or shape of objects in the plurality of images to an average size or shape of blood cells.

In a general embodiment, a device for analyzing a polymerase chain reaction in a fluid sample includes a current source configured to cause the polymerase chain reaction by heating the fluid sample within a target zone, a camera imaging device configured to record a plurality of images of the fluid sample in the target zone while the current source causes the polymerase chain reaction, and a controller configured to analyze the plurality of images by (i) dividing the target zone shown in the plurality of images into a plurality of bins, (ii) selecting at least two of the plurality of bins, and (iii) calculating a fluorescence value of the selected at least two of the plurality of bins.

In an example embodiment, the controller is configured to select the at least two of the plurality of bins based on a threshold value for brightness.

In an example embodiment, the controller is configured to exclude at least one of the plurality of bins from the fluorescence value calculation if the at least one of the plurality of bins overlaps an unwanted object.

In an example embodiment, the controller is configured to assign weights to the selected at least two of the plurality of bins for the calculation based on the proximity of the selected at least two of the plurality of bins to an unwanted object.

In a general embodiment, a method of analyzing a polymerase chain reaction in a fluid sample includes heating the fluid sample in a target zone to cause the polymerase chain reaction, recording a plurality of images of the fluid sample in the target zone during the polymerase chain reaction, dividing the target zone into a plurality of bins, calculating a fluorescence value of at least two of the plurality of bins, and determining whether the fluid sample tests positive or negative for a bacteria or virus based on the calculated fluorescence value.

In an example embodiment, calculating the fluorescence value includes weighting the at least two of the plurality of bins based on proximity to an unwanted object.

In an example embodiment, calculating the fluorescence value includes excluding at least one of the plurality of bins from the fluorescence value calculation if the at least one of the plurality of bins overlaps an unwanted object.

In an example embodiment, calculating the fluorescence value includes excluding at least one of the plurality of bins based on a threshold value for brightness.

In a general example embodiment, a device for analyzing a fluid sample includes a camera imaging device configured to record a plurality of images of the fluid sample while located within a target zone of a fluid microchannel, and a controller configured to (i) distinguish wanted objects in the plurality of images from an unwanted object in the plurality of images, and (ii) determine whether the fluid sample tests positive or negative for a bacteria or virus based on the wanted objects.

In an example embodiment, the controller is configured to determine whether the fluid sample tests positive or negative for the bacteria or virus by dividing the target zone shown in the plurality of images into a plurality of bins, selecting at least two of the plurality of bins, and calculating a fluorescence value of the selected at least two of the plurality of bins.

BRIEF DESCRIPTION OF THE DRAWINGS

Embodiments of the present disclosure will now be explained in further detail by way of example only with reference to the accompanying figures, in which:

FIGS. 7A to 7E illustrate an example embodiment showing how a controller can detect bubbles and analyze a reaction even when bubbles are detected;

DETAILED DESCRIPTION

Before describing in detail the illustrative system and method of the present disclosure, it should be understood and appreciated herein that the present disclosure relates to a rapid, high sensitivity and high specificity, low complexity, diagnostic system 1 using nucleic acid amplification and capable of operating in low resource settings with minimal user training. The system described herein is configured, for example, to cause and analyze polymerase chain reactions (PCR), particularly in the early stages of infection, using a low-cost microfluidic platform employing PCR with a modified DNA polymerase.

Figure 1:
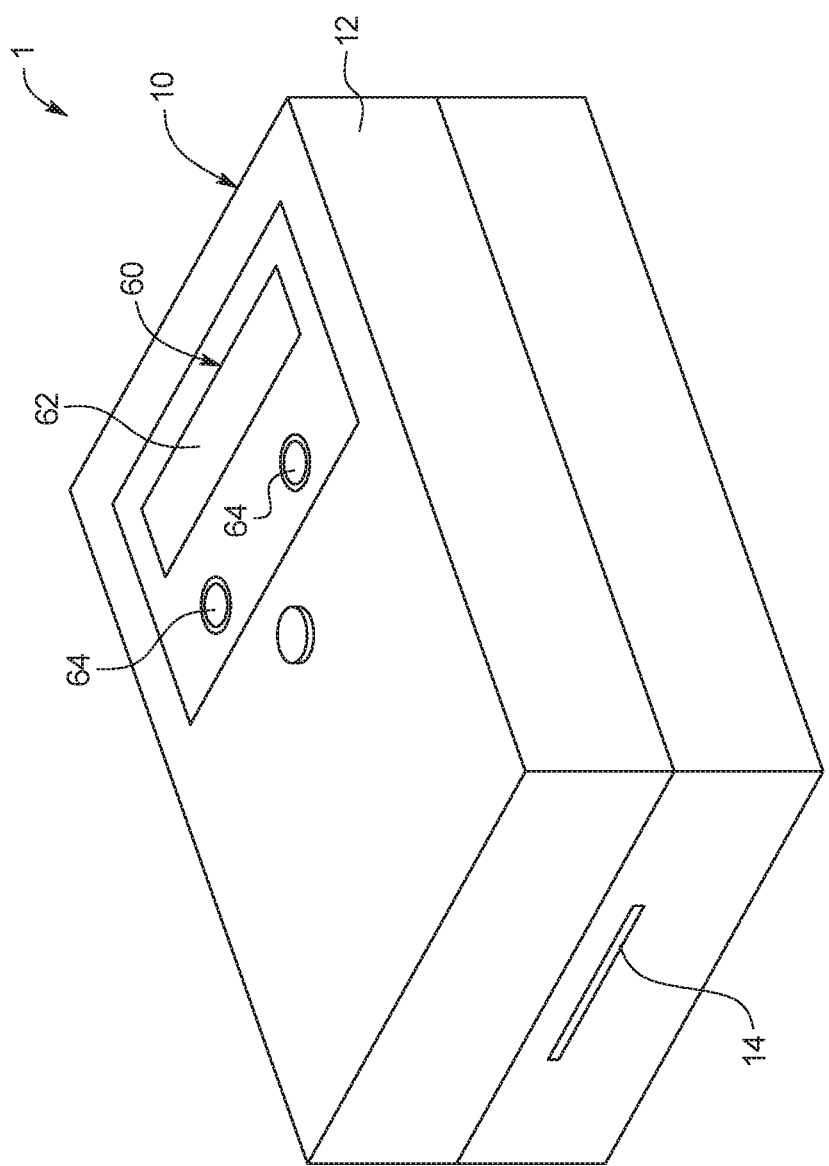
FIG. 1 is a top perspective view of an example embodiment of an assay device according to the present disclosure.

FIG. 1 illustrates an example embodiment of a point-of-care diagnostic system 1 according to the present disclosure. As illustrated, diagnostic system 1 includes an assay device 10 with a housing 12 having a slot 14 to receive a test card 100 (FIG. 2), which is an inexpensive, disposable test card that can be used with device 10 and then discarded. As explained in more detail below, a fluid sample can be injected into test card 100, and then test card 100 can be inserted into slot 14 so that device 10 can power test card 100 to run an assay within test card 100 without further action by the user. The resulting analysis can then be displayed to the user by user interface 60. Test card 100 can then be discarded and a new test card 100 can be inserted into slot 14 and used the same way to run a new assay. In an embodiment, the test card is configured to receive about 10 µL of whole blood, the equivalent to a drop of blood obtained from a finger stick. In another embodiment, the fluid sample can be serum, urine, saliva, tears and/or the like.

Device 10 is described in more detail in U.S. application Ser. No. 15/185,640, entitled "Device for Analyzing a Fluid Sample and Use of Test Card with Same", filed concurrently herewith, the entire disclosure of which, and specifically the device and test card structure disclosure, is incorporated herein by reference and relied upon. Those of ordinary skill in the art will recognize other configurations of device 10 that can be used according to the present disclosure.

Test card 100 is described in more detail in U.S. application Ser. No. 15/185,661, now U.S. Pat. No. 10,214,772, entitled "Test Card for Assay and Method of Manufacturing Same", filed concurrently herewith, the entire disclosure of which, and specifically the test card structure disclosure, is incorporated herein by reference and relied upon. Those of ordinary skill in the art will recognize other configurations of test card 100 that can be used according to the present disclosure.

Figure 2:
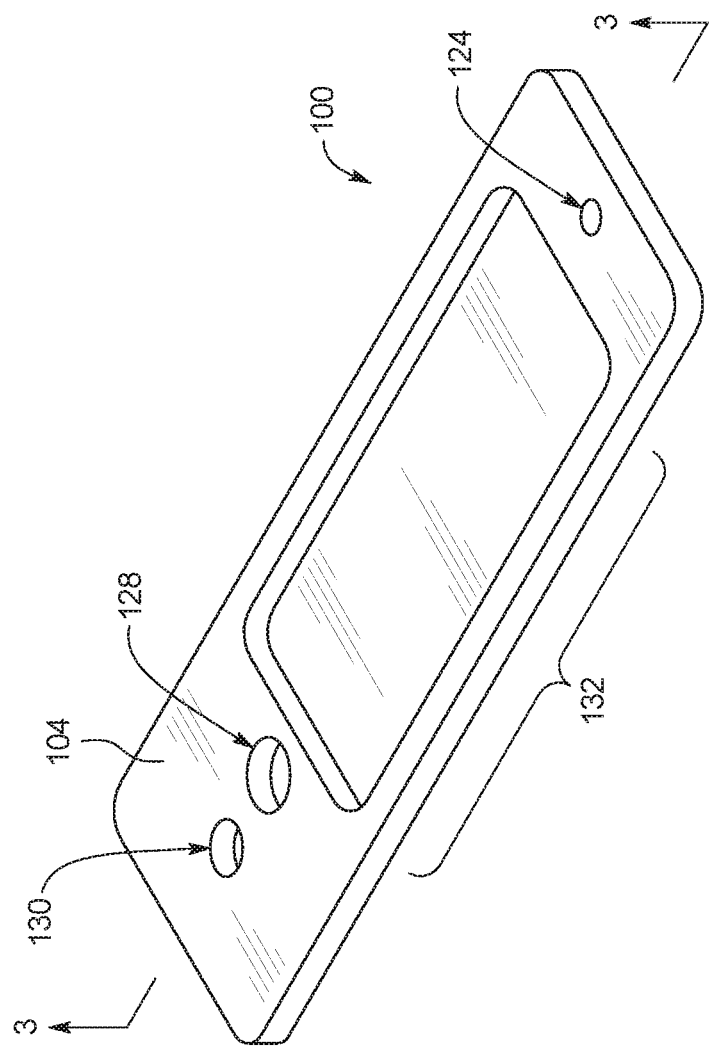
FIG. 2 is a top perspective view of an example embodiment of a test card according to the present disclosure.
Figure 3:
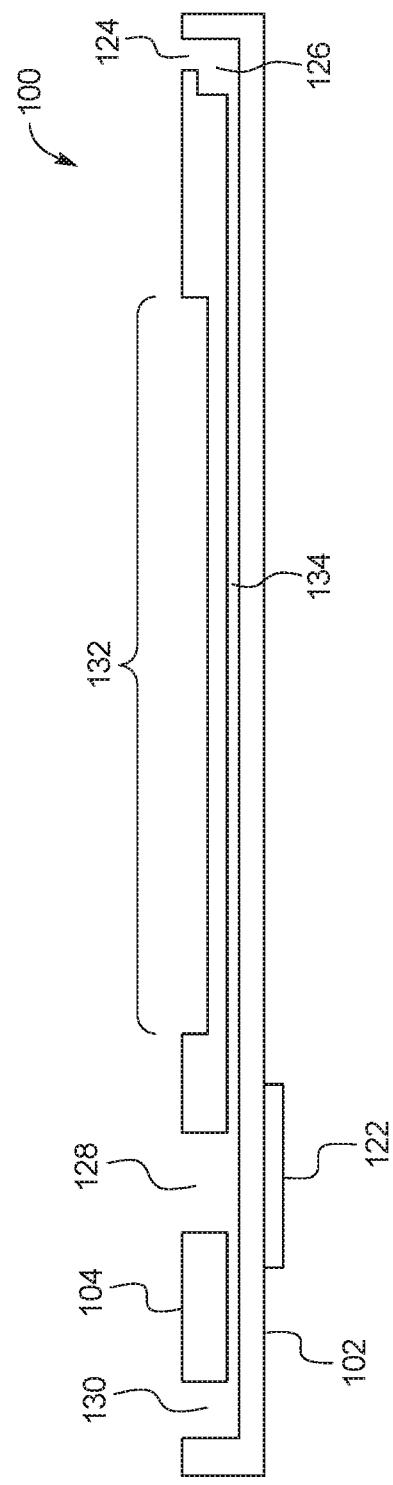
FIG. 3 is a cross-sectional view of the test card of FIG. 2.

As illustrated in FIGS. 2 and 3, test card 100 includes an inlet port 124, a mixing chamber 126, a capture port 128, an outlet port 130, and a fluid microchannel 134. A liquid sample can be injected into inlet port 124 and mixed with one or more reagent in mixing chamber 126, and then test card 100 can be placed into slot 14 of assay device 10. Once test card 100 has been placed within device 10, the fluid sample can be pulled though fluid microchannel 134, so that the fluid sample can be analyzed through an analysis port 132 of test card 100. Test card 100 also includes electrical contacts 122 on a bottom surface 102 thereof, which enables electrodes adjacent to fluid microchannel 134 to be controlled to power test card 100, for example, to heat fluid within fluid microchannel 134, track fluid flow through fluid microchannel 134 and/or measure the concentration of a chemical species in the fluid sample.

Figure 4:
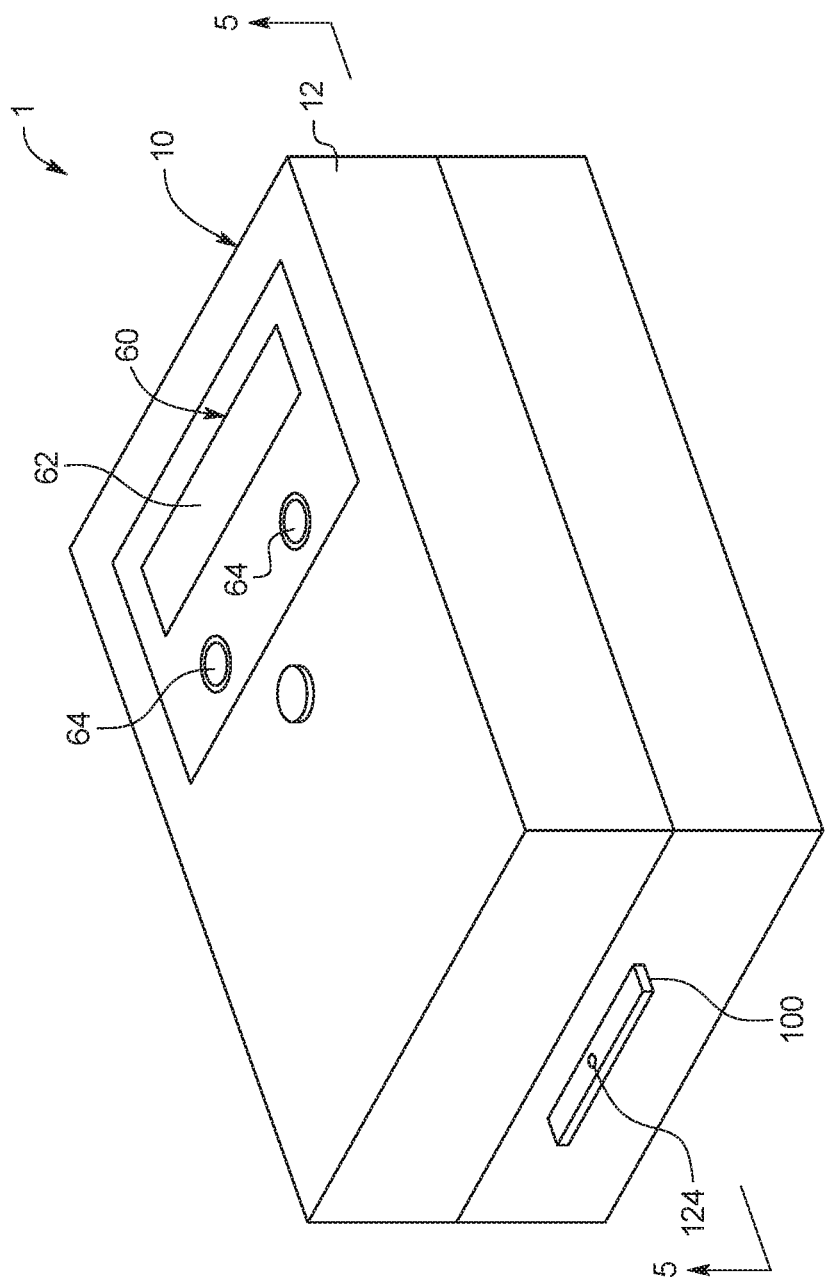
FIG. 4 is a top perspective view of the assay device of FIG. 1 with the test card of FIG. 2 inserted therein.
Figure 5:
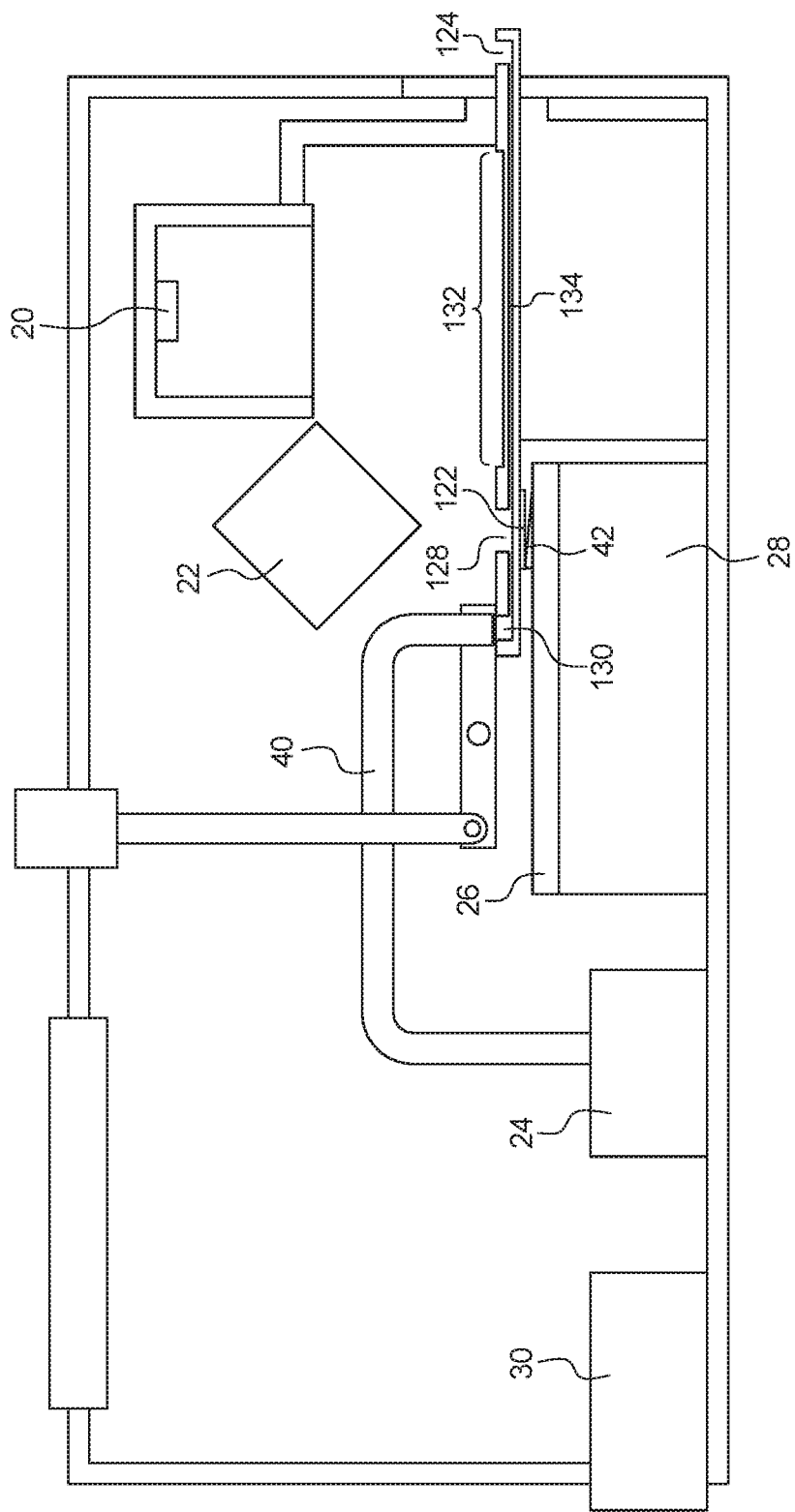
FIG. 5 is a cross-sectional view of the assay device and test card shown in FIG. 4.

FIG. 4 illustrates a perspective view of device 10 after test card 100 has been placed into slot 14, and FIG. 5 illustrates a cross-sectional view thereof. As illustrated, placement of test card 100 into slot 14 aligns several of the elements of device 10 with several of the elements of test card 100. For example, placement of test card 100 into slot 14 aligns camera imaging device 20 and light source 22 of device 10 with analysis port 132 on an upper surface 104 of test card 100, pneumatic tube 40 of fluid actuation source 24 with outlet port 130 on the upper surface 104 of test card 100, and electrical contacts 42 of electrical contact device 26 with electrical contacts 122 on the bottom surface 102 of test card 100.

As explained in more detail in U.S. application Ser. No. 15/185,640, once pneumatic tube 40 is sealed against outlet port 130, a negative pneumatic force can be applied to outlet port 130 from fluid actuation source 24. When the negative pneumatic force is applied, the fluid sample injected into inlet port 124 is pulled through fluid microchannel 134 towards outlet port 130. The fluid sample however is not pulled into pneumatic tube 40 due to the presence of capture port 128 between inlet port 124 and outlet port 130. Capture port 128 allows fluid to build up before it can reach outlet port 130 and/or pneumatic tube 40, which keeps device 10 sterile and protects the integrity of diagnostic system 1.

Test card 100 is dimensioned so that electrical contacts 122 of test card 100 are placed into electrical contact with electrical contacts 42 of electrical contact device 26 when test card 100 is fully inserted into slot 14. With the electrical contacts 42 and 122 aligned, controller 28 can perform several functions. Before beginning an assay, controller 28 can ensure that the fluid sample has been properly pulled through microchannel 134 and into a target zone of microchannel 134 by measuring the capacitance of the fluid sample upstream and/or downstream of the target zone. Once it is determined that fluid is located within the target zone of microchannel 134, controller 28 can control power source 30 to apply a current to electrical contacts aligned with the target zone to heat the fluid sample located within target zone and cause a reaction such as a PCR to occur.

The alignment of camera imaging device 20 over analysis port 132 on the upper surface 104 of test card 100 allows controller 28 to analyze one or more reaction within fluid microchannel 134 while controlling the reaction. Camera imaging device 20 is configured to record a plurality of images of the fluid sample within the target zone so that the images can be analyzed in real time. The plurality of images can include, for example, a plurality of still images and/or a video image. Camera imaging device 20 is therefore configured to record the reaction of the fluid sample by taking a series of still images of the fluid sample within the target zone during a reaction or by taking a video of the fluid sample within the target zone during a reaction. As explained in more detail below, the plurality of images can be used, for example, to analyze the physical and/or chemical characteristics of cells within the fluid sample.

The target zone can be anywhere along fluid microchannel 134 or can be branched off of fluid microchannel 134. Example embodiments of target zones are described in more detail in U.S. application Ser. No. 15/185,661, now U.S. Pat. No. 10,214,772, entitled "Test Card for Assay and Method of Manufacturing Same", filed concurrently herewith. In an embodiment, the target zone can be located at a central portion of fluid microchannel 134 and fluid microchannel 134 can include, for example, a capacitance sensor upstream and/or downstream of the target zone to determine whether fluid has been pulled through fluid microchannel 134 and into the target zone. In an embodiment, microchannel 134 can include a plurality of target zones to perform a plurality of assays at the same or different times, for example, to improve the reliability of the assays. In an embodiment, controller 28 can be programmed to analyze a specific section of microchannel 134 as the target zone, or controller 28 can determine the target zone based on the plurality of images taken by camera imaging device 20.

Figure 6A:
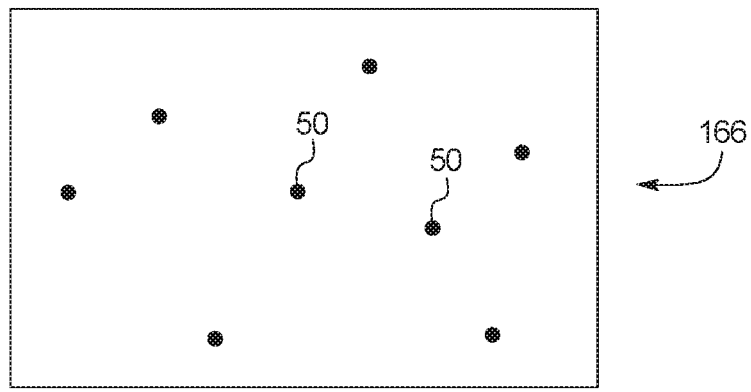
FIGS. 6A to 6C illustrate an example embodiment of amplified images showing a PCR.
Figure 6B:
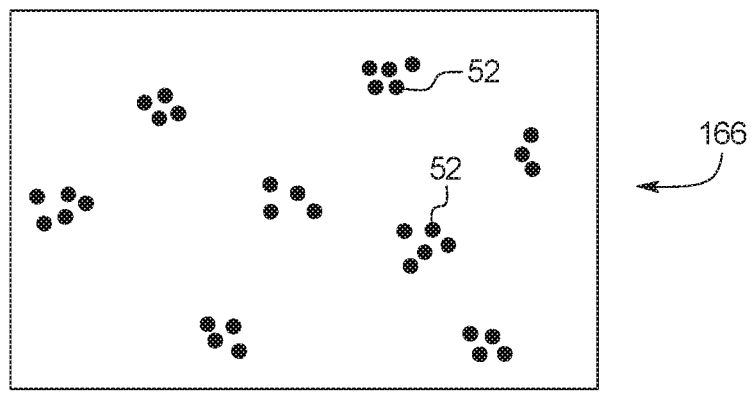
Figure 6C:
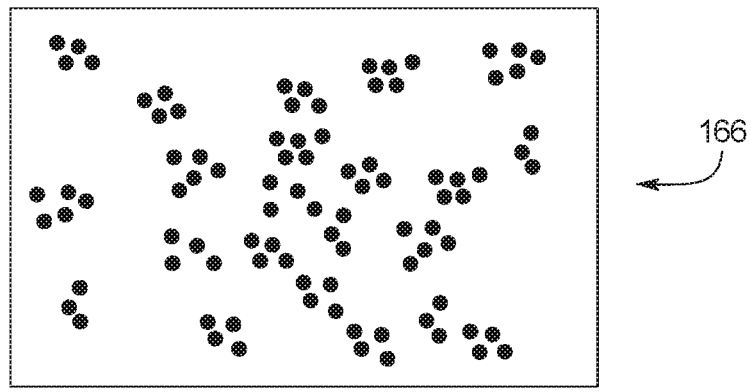

FIGS. 6A to 6C illustrate an example embodiment of amplified images showing a PCR. FIG. 6A illustrates a fluid sample that has been initially loaded into target zone 166, with a few nucleic acid molecules 50 separated by large distances. FIG. 6B shows the fluid sample during the PCR, when clear colonies 52 of nucleic acid molecules 50 can be viewed because the diffusion speed of the molecules is slower than the speed required for the molecules to travel the distance between colonies. FIG. 6C shows the end of the PCR, when the colonies 52 are no longer clearly visible.

From the number of colonies shown in FIG. 6B, controller 28 can determine whether the fluid sample tests positive or negative for a specific virus or bacteria based on a known titer value for the specific virus or bacteria. The titer value corresponds to the highest dilution factor for the specific virus or bacteria that yields a positive test result. By counting the colonies in FIG. 6B, and by comparing the count with the known titer value, controller 28 can determine a positive or negative test result for the fluid sample. The known titer value can be compared through a variety of methods. In an embodiment, a statistical analysis can be utilized to say with certain probability that the result will fall under a certain titer value. This can be achieved by running a statistically significant amount of controlled samples under controlled dilutions and generate a standard curve based on the crossover threshold value of each (point at which the curve starts to increase).

In an embodiment, camera imaging device 20 includes a high sensitivity and dynamic range complementary metal-oxide semiconductor (CMOS) camera sensor which allows for general imaging of a reaction within target zone 166 of fluid microchannel 134 of test card 100. In an embodiment, the CMOS camera sensor enables camera imaging device 20 to image the entire analysis port 132 of test card 100. Although in the illustrated embodiment only a single target zone 166 within a single microchannel 134 is shown, camera imaging device 20 is configured to image a plurality of target zones and/or a plurality of microchannels should the user insert such a test card 100 into device 10. Examples of alternative embodiments of test cards 100 are disclosed in U.S. application Ser. No. 15/185,661, now U.S. Patent No. 10,214,772, entitled "Test Card for Assay and Method of Manufacturing Same", filed concurrently herewith.

In the illustrated embodiment, light source 22 is configured to project a fluorescent excitation light on target zone 166 of fluid microchannel 134 during a PCR, while camera imaging device 20 is recording still and/or video images of the PCR. In an embodiment, the fluid sample has been mixed with a fluorescence reagent in mixing port 126, before the fluid sample is pulled into target zone 166. By illuminating target zone 166 with a fluorescence excitation light, controller 28 can record fluorescence measurements from the images taken by camera imaging device 20. The fluorescence images can be analyzed to determine the incremental increases in fluorescence during each PCR cycle. This allows the determination of the PCR amplification curve. Additionally, the images can be used during melt analysis to determine the incremental decrease in fluorescence as temperature is increased. Incremental change in fluorescence can be determined by taking the difference in pixel intensity between successive images.

For general fluorescence measurements, for example, a statistical formulation of the PCR can be achieved by subdividing the target zone 166 and measuring florescence at various locations in the target zone 166. This yields highly-accurate and consistent crossover threshold values for the real-time PCR based on titer values. Once the PCR is complete, a melting curve analysis allows for error checking, ensuring that the correct amplicon has been amplified during the PCR, to reduce the likelihood of a false-positive test.

Camera imaging device 20 also enables controller 28 to record a variety of other measurements in addition to fluorescence measurements. For example, controller 28 can determine turbidity and object detection using the images taken by camera imaging device 20. The turbidity can be determined by using the device LEDs to apply incident light to a test card microchannel and/or target zone. The amount of scattered light can be measured by the camera allowing a numerical value of relative turbidity to be measured. The turbidity can be used to determine the outcome of various different reactions, such as measuring the reactiveness of proteins during an ELISA test (colorimetry measurement) or measurement of water quality. The object detection can be used, for example, to determine whether air bubbles formed in target zone 166 during the PCR and potentially destroyed the integrity of the PCR analysis. By imaging the entire analysis port 132 of test card 100, camera imaging device 20 is able to greatly improve accuracy by allowing for various advanced image-processing algorithms to be applied.

With respect to object detection, camera imaging device 20 can be used to detect both wanted and unwanted objects within microchannel 134. In an embodiment, the wanted objects are cells such as red and white blood cells in the fluid sample to be analyzed during the reaction. Controller 28 can count the wanted objects by matching the cell size and cell shape of objects in the images from camera imaging device 20 to the average size and shape of specific blood cells, allowing controller 28 to count, for example, the number of red and white blood cells in the fluid sample at target zone 166. Controller 28 can also distinguish the red and white blood cells from other unwanted objects that do not match the average size and shape of specific blood cells.

If controller 28 detects an unwanted object, controller 28 can determine that the PCR has failed or is indeterminate, and can instruct a user that an additional PCR should be run on the same or a different test card. If the PCR is run on the same test card, target zone 166 should be cleared of fluid, and then new fluid should be pulled from mixing chamber 126 into target zone 166.

In an embodiment, the unwanted image is an air bubble. In an embodiment, controller 28 can detect air bubbles because air bubbles will expand in the target zone 166 while the PCR reaction occurs. Red and white blood cells, on the other hand, multiply but do not increase in size. Controller 28 can therefore determine the presence of an air bubble in target zone 166 by noting a change in size of an object across a plurality of subsequent images from the plurality of images. In another embodiment, controller 28 can determine the presence of an air bubble by noting that an unwanted object does not match the average size and shape of blood cells. In another embodiment, controller 28 can determine the presence of an air bubble due to there being no fluorescence inside of the bubble by looking for a change in the gradient of fluorescence.

In some cases, a bubble formed within microchannel 134 will remain small and will not affect any fluid flow or reaction occurring within microchannel 134. When heat is applied to target zone 166, however, the heat can cause the bubble to expand due to the large thermal expansion coefficient of the bubble.

FIGS. 7A to 7E illustrate an example embodiment showing how controller 28 can detect unwanted objects such as bubbles and analyze a reaction even when bubbles are present. In some cases, unwanted objects may cause the reaction to fail completely and need to be rerun. A failure might occur if there are too many bubbles to compensate for. In FIGS. 7A to 7E, however, controller 28 can proceed with the reaction and analysis even with an air bubble present.

Figure 7A:
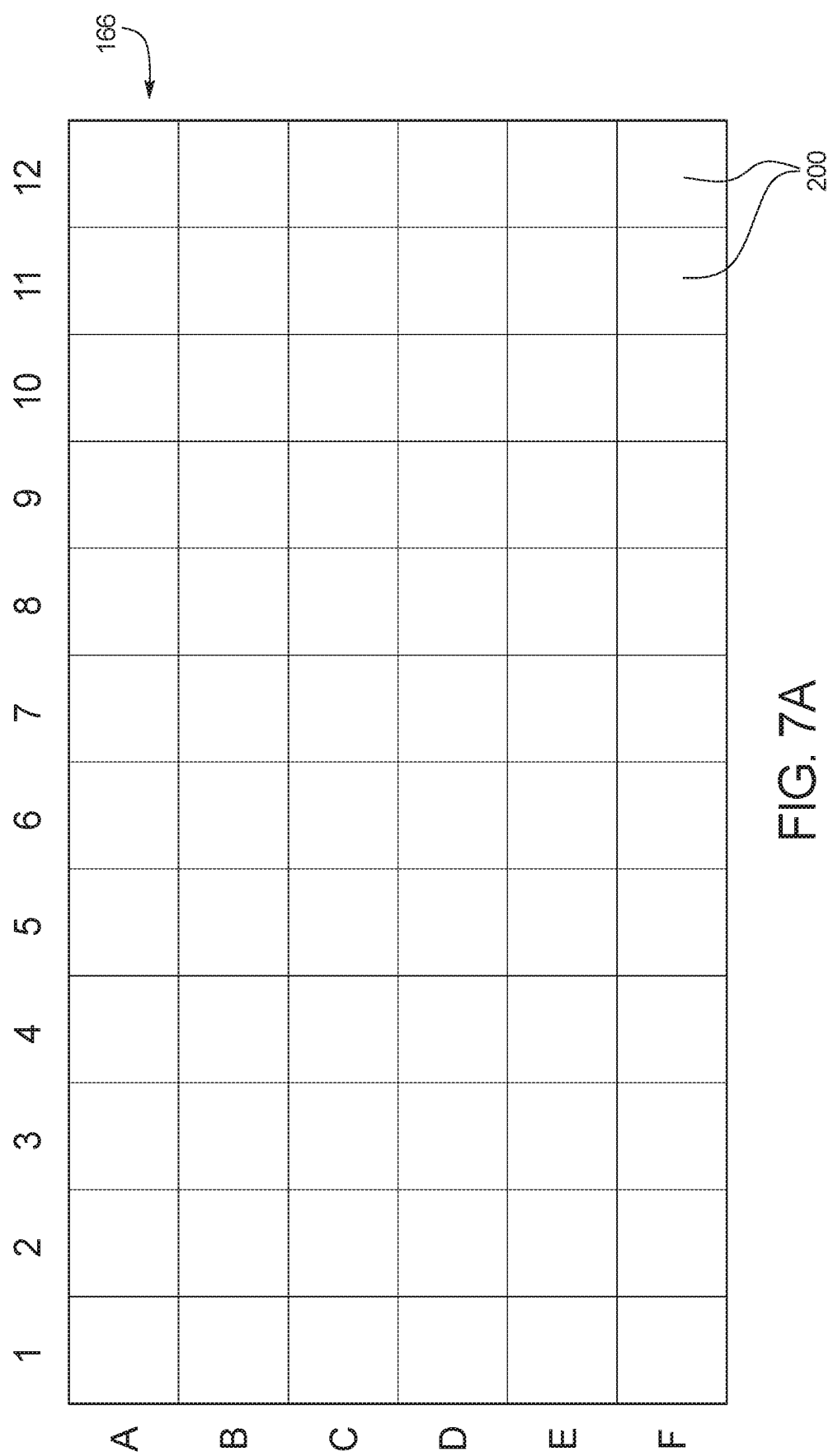

FIG. 7A illustrates an example embodiment of target zone 166 before any fluid has entered the target zone. As illustrated, controller 28 has divided target zone 166 into a plurality of bins 200. In the illustrated embodiment, controller 28 has divided target zone 166 into six rows (labeled A to F for ease of reference) and twelve columns (labeled 1 to 12 for ease of reference) to create seventy-two bins 200, but those of ordinary skill in the art will recognize that any number of bins 200 can be created within a target zone 166. It should be understood that the bins 200 are created virtually by controller 28, and there are no physical barriers separating the bins 200 within target zone 166.

Figure 7B:
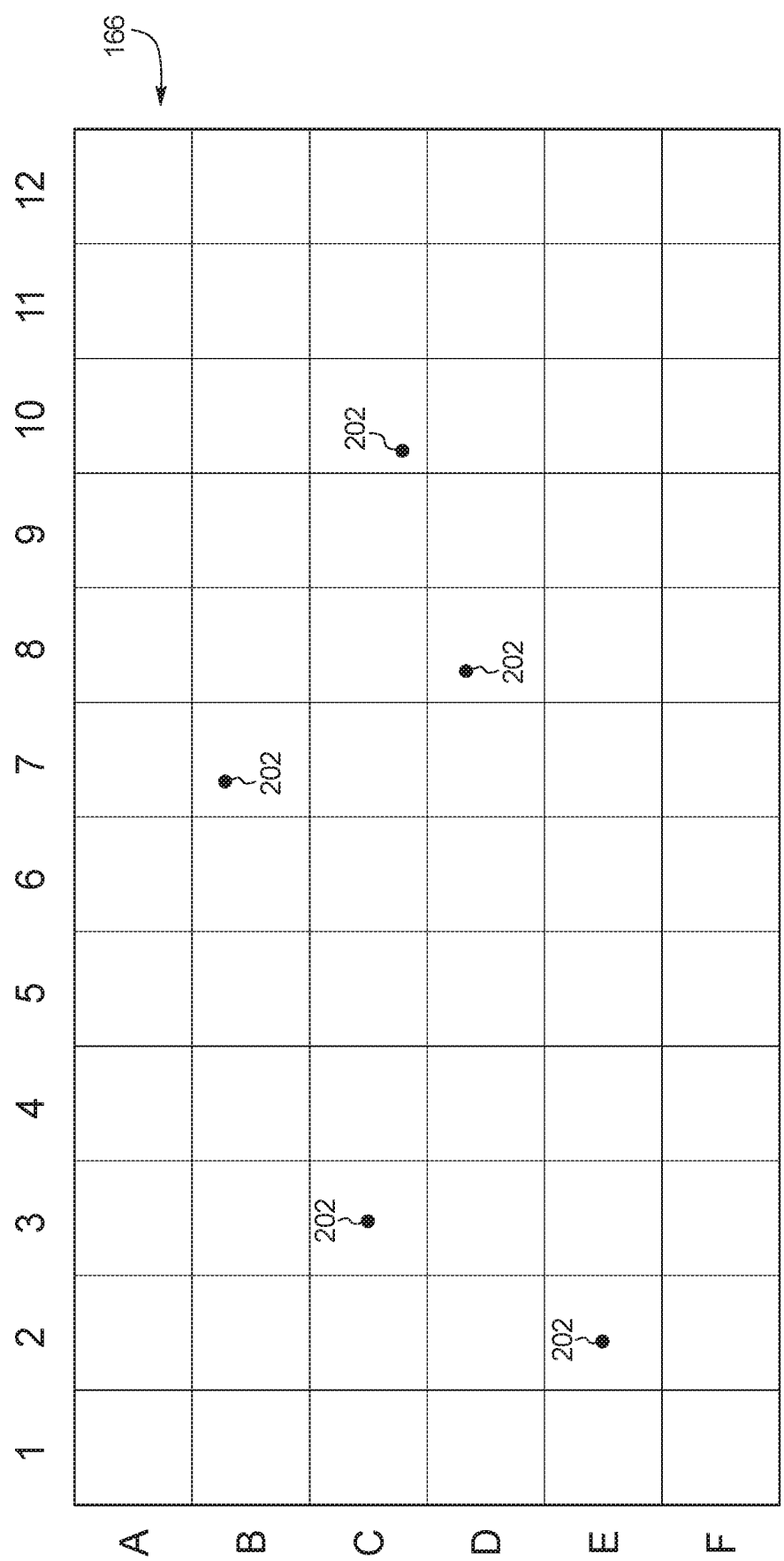

FIG. 7B illustrates target zone 166 after receiving a fluid sample but before a reaction has occurred. As illustrated, there are a minimal number of nucleic acid molecules 202 in the fluid sample before the reaction. In the illustrated embodiment, bins B7, C3, C10, D8 and E2 contain nucleic acid molecules 202.

Figure 7C:
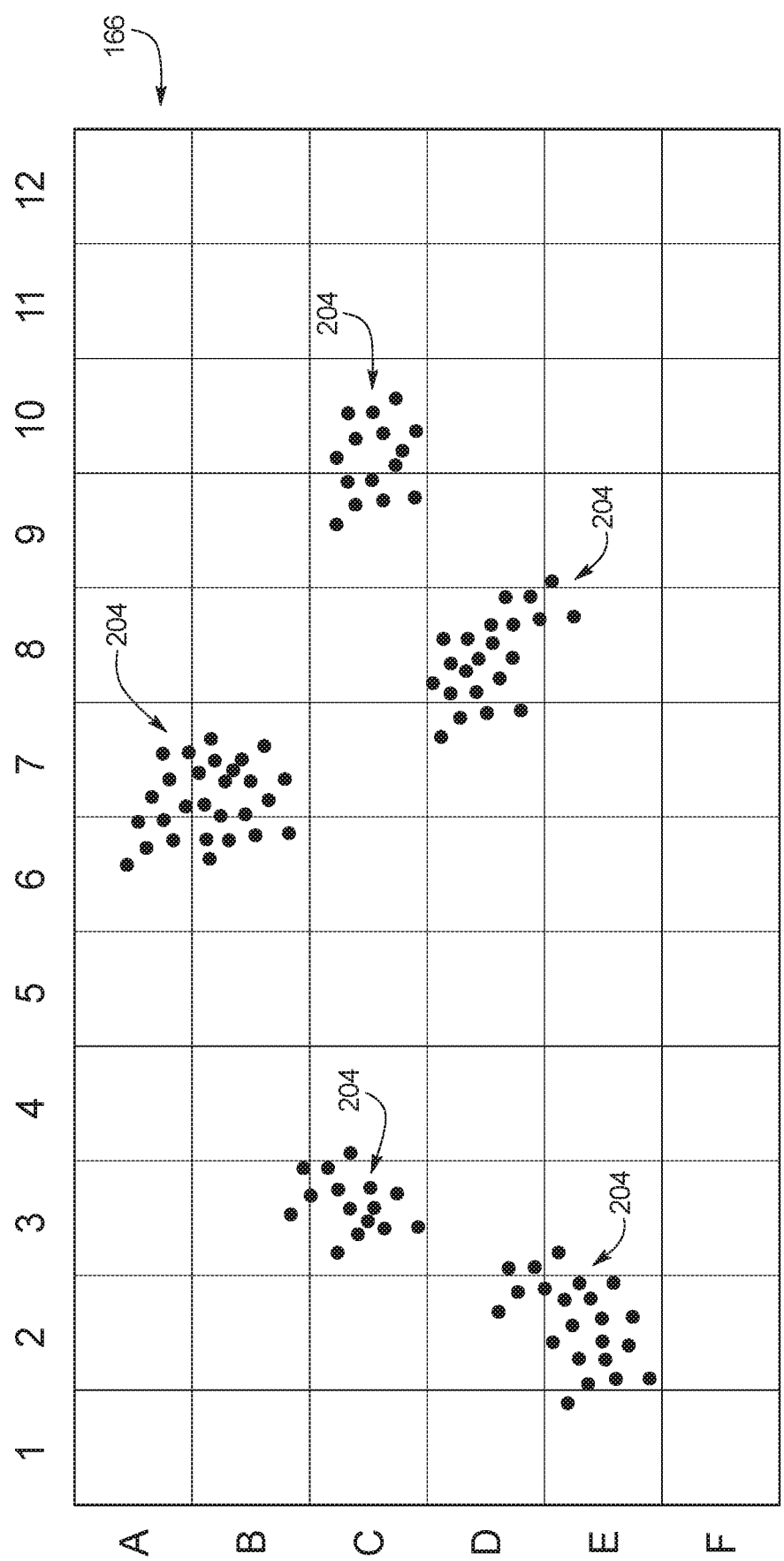

FIG. 7C illustrates target zone 166 during a PCR. As illustrated, the molecules shown in bins B7, C3, C10, D8 and E2 in FIG. 7B have multiplied by diffusion. Clear colonies 204 of nucleic acid molecules 202 can be viewed because the diffusion speed of the molecules is slower than the speed required for the molecules to travel the distance between colonies. Bins A6, A7, B3, B6, B7, C3, C4, C9, C10, D2, D3, D7, D8, E1, E2, E3, E8 and E9 each contain nucleic acid molecules 202 in FIG. 7C.

Figure 7D:
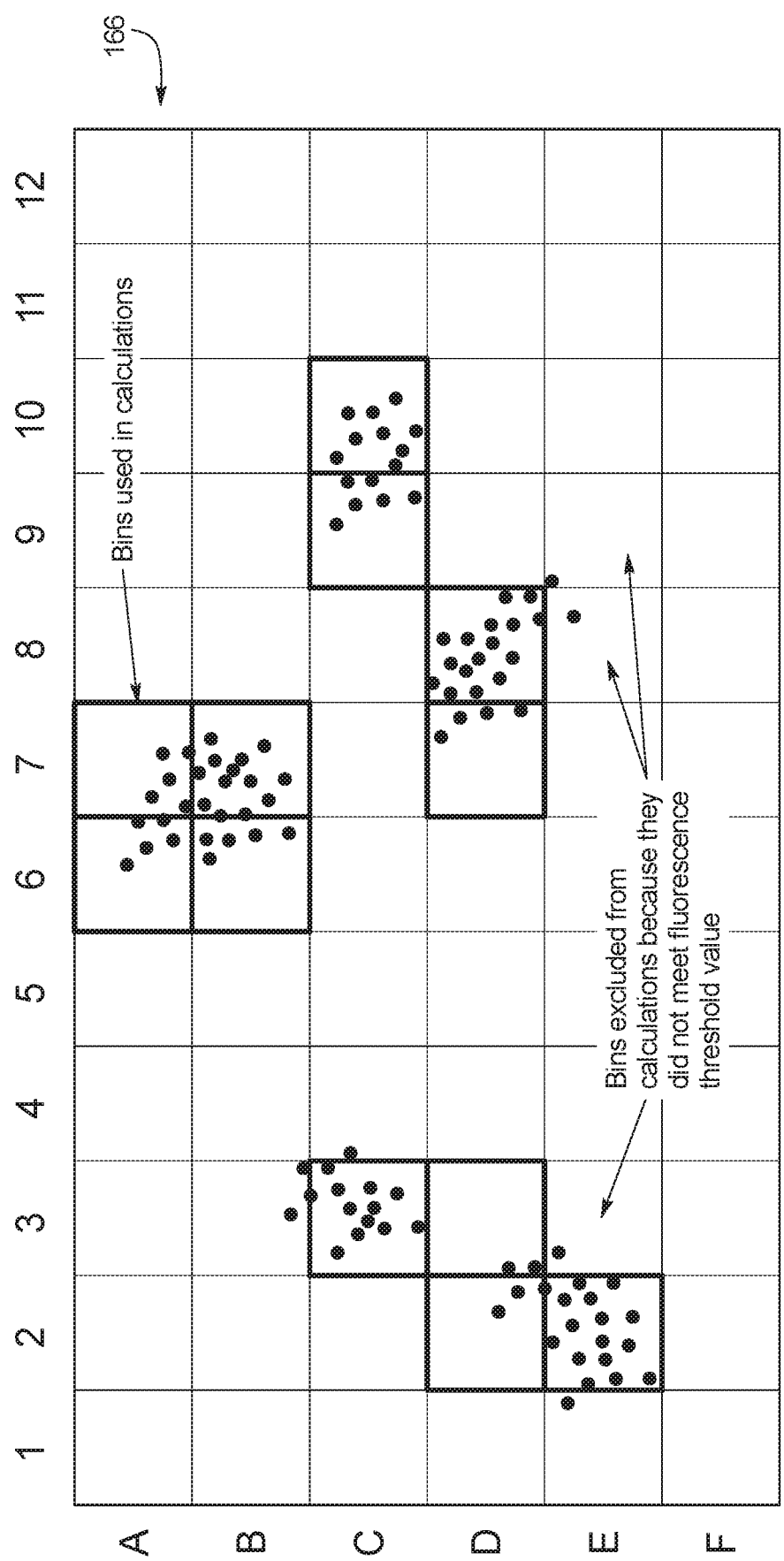

FIG. 7D illustrates bins 200 that have been selected by controller 28 to be used in calculations for amplification and melt curves and for the corresponding analysis. In the illustrated embodiment, the colonies 204 of nucleic acid molecules 202 are visualized by controller 28 based on localized increases in brightness in each bin. If a bin 200 reaches a threshold value for brightness, then that bin's fluorescence value is used in calculations for amplification and melt curves and for the corresponding analysis. If a bin 200 does not reach the threshold value for brightness, then that bin 200 is excluded from the calculations for amplification and melt curves and for the corresponding analysis. In order to get a final value for fluorescence of the entire target zone 166, the arithmetic mean is taken between all of the selected bins 200. In the illustrated embodiment, bins A6, A7, B6, B7, C3, C9, C10, D2, D3, D7, D8 and E2 have been selected for use in calculations for amplification and melt curves and for the corresponding analysis, while bins B3, C4, E1, E3, E8 and E9 have been excluded even though they contain nucleic acid molecules because they do not meet the threshold for brightness.

FIG. 7E illustrates how an unwanted object such as a bubble affects the analysis by controller 28. In the illustrated embodiment, a bubble 206 has been detected by controller 28 in bins C3, C4, C5, C6, D3, D4, D5, D6, E3, E4, E5, E6, F3, F4 and F5. Even though bins C3 and D3 met the threshold value for brightness, controller 28 has determined that bins C3 and D3 should be excluded from the amplification and melt curves and corresponding analysis due to the presence of bubble 206. Controller 28 has also determined that bins D2 and E2 should be given a lower weight during calculations due to their proximity to bubble 206.

Based on the above analysis, controller 28 can average the fluorescence values of the selected bins 200. If controller 28 does not detect any bubbles in the images taken by camera imaging device 20, then controller 28 calculates the fluorescence using the following equation:

$$F = \frac{\sum_{i=1}^{n} x_i}{n},$$

wherein n is the number of bins 200 used in the calculation, and $x_i$ is the individual bins in the grid utilized by the algorithm.

If one or more bubble is detected in target zone 166, then controller 28 calculates the fluorescence using the following equation:

$$F = \frac{\sum_{i=1}^{n} a_i x_i}{n},$$

where $a_i$ is the bin's weight, which is determined by the bin's proximity to the bubble. In an embodiment, $a_i$ should be greater than zero and less than or equal to one ($0 < a_i \leq 1$).

In an embodiment, the $a_i$'s may all have an equal weight of 1 when there are no bubbles present. In an embodiment, the $a_i$'s value can decrease proportionally as the bubble gets closer to the bin.

In an embodiment, the amplification curve and melt curve are created by measuring the absolute value of the fluorescence of each pixel in successive images taken either during each cycle (for the amplification curve) or as temperature is slowly increased over time (for the melt curve). In the case of an amplification curve, which shows the incremental change in fluorescence during the amplification stage of a PCR, a PCR crossover threshold value can be determined, and controller 28 can look for when the fluorescence value has increased past a certain threshold value and when the first derivative of fluorescence with respect to cycle number is at a maximum. In the case of a melt curve, the incremental change in fluorescence can give controller 28 the melting temperature of the amplified DNA. Mathematically, controller 28 looks for when the first derivative of the fluorescence with respect to temperature is at a minimum, and the second derivative of the fluorescence with respect to temperature is equal to zero.

The above detection and analysis is useful for a fluorescence based PCR or cytometry analysis, but those of ordinary skill in the art will recognize that controller 28 can be used for other purposes. In an embodiment, controller 28 can use camera imaging device 20 to perform a colormetric analysis, which analyzes the concentration of a chemical element or chemical compound in a solution with the aid of a color reagent. Controller 28 can quantify the amount of protein present in the fluid sample by measuring the absorption spectra and comparing it with protein solutions of known concentration. In an embodiment, controller 28 can analyze and interpret the results of colormetric protein assays, for example, a Bradford protein assay, a bichinchoninin acid assay (BCA assay), and/or a Ponceau S dye assay.

Figure 8:
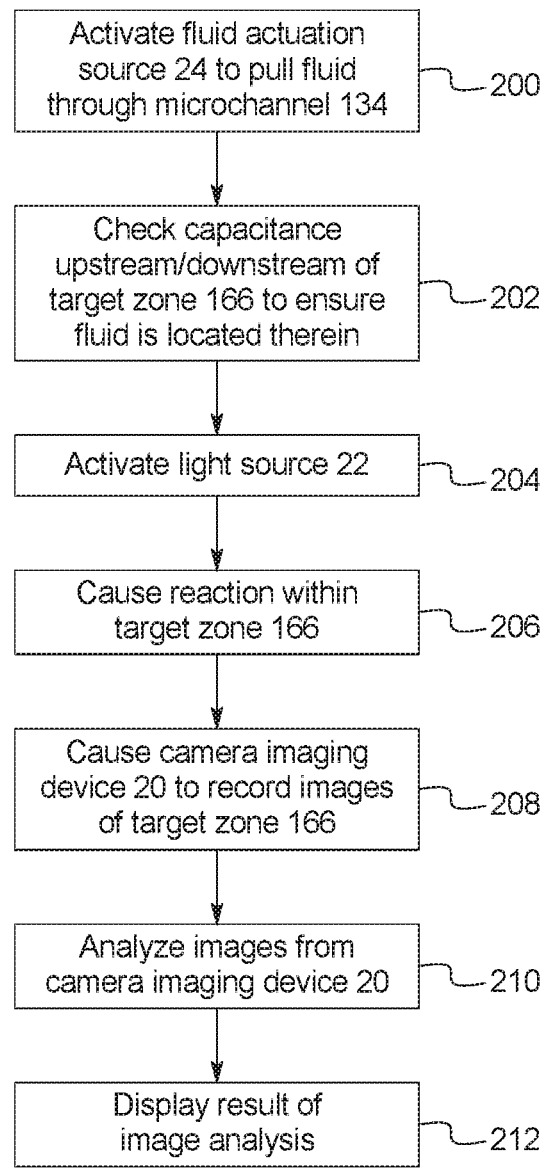
FIG. 8 illustrates an example embodiment of a control method that can be used to perform and analyze a reaction according to the present disclosure.
Figure 9:
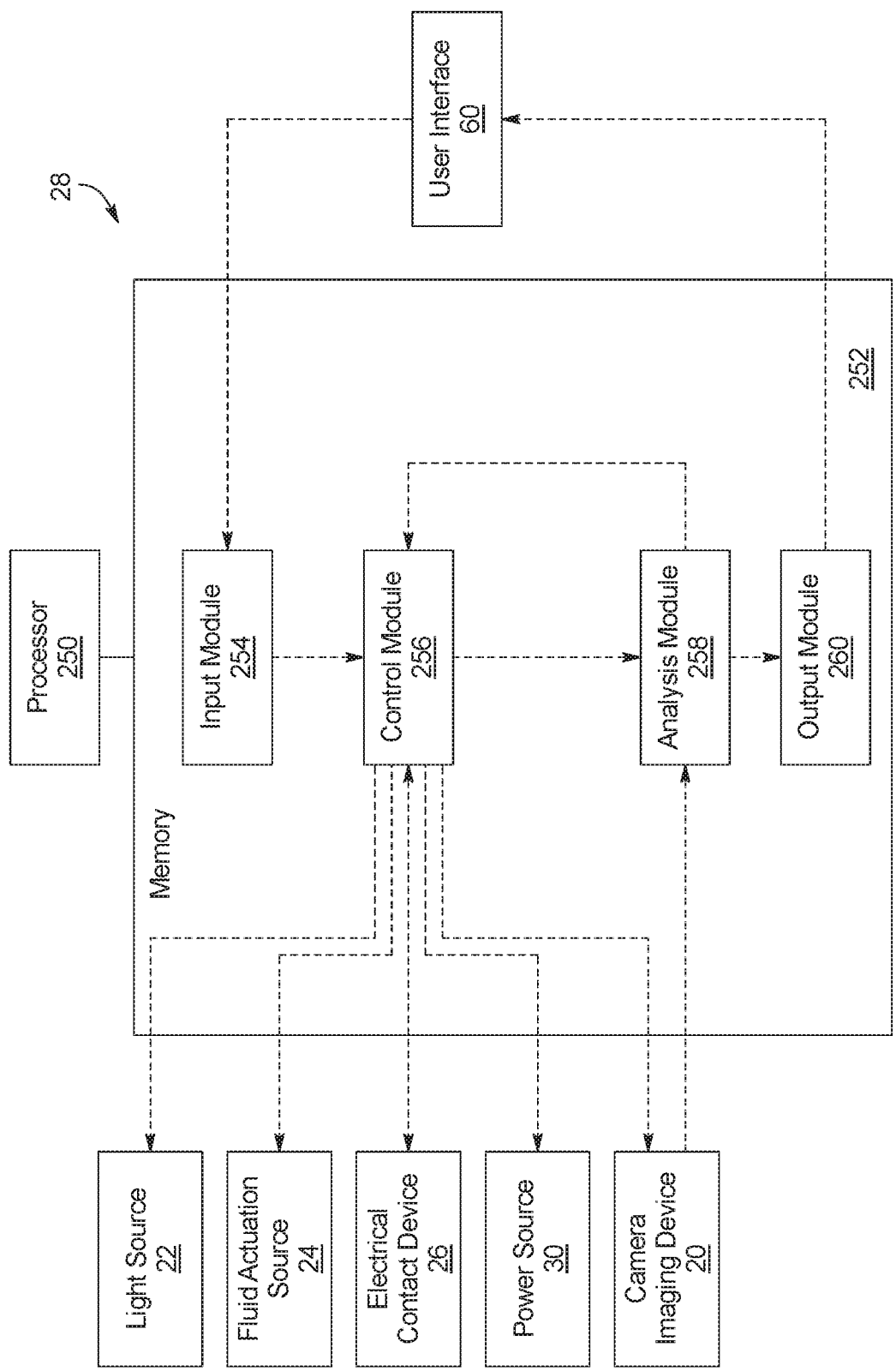
FIG. 9 illustrates an example embodiment of a controller that can perform the method of FIG. 8.

FIG. 8 illustrates an example embodiment of a control method that can be used by controller 28 to perform and analyze a reaction as described herein, and FIG. 9 illustrates an example embodiment of a controller 28 that can perform the method of FIG. 8. As illustrated, controller 28 can include a processor 250 and a memory 252, which can include a non-transitory computer readable medium. Memory 252 can include, for example, an input module 254, a control module 256, an analysis module 258, and an output module 260. Processor 250 can run the modules 252, 254, 256, 258 in accordance with instructions stored on memory 252. The broken lines in FIG. 8 illustrate the electrical connections between the modules 252, 254, 256, 258 of controller 28 and various elements of device 10. It should be understood by those of ordinary skill in the art that the illustrated modules and/or additional modules can be connected to the elements shown and/or additional elements.

The process begins by loading a test card 100 and/or a fluid sample into device 10. The fluid sample can be mixed with a reagent before injection into test card 100 and/or device 10, or can be mixed with a reagent within mixing chamber 126 of test card 100. In an embodiment, the reagent includes a PCR inhibitor-resistant polymerase along with a specific mixture of reverse transcriptase (in the case of RNA targets) and surfactants/dispersants to allow for rapid sample dispersion and lysing. In an embodiment, the reagent mix can include, for example, olignucleotide primers, dNTP's DNA polymerase and other chemicals to assist the PCR. It is important to have a correct ratio of fluid sample to final PCR volume, because if the correct ratio is not maintained, the PCR will take too long or fail.

Using user interface 60, a user can then choose a positive/negative test to run on the fluid sample. In an embodiment, the user can cycle through a plurality of tests on display 62 using buttons 64 and choose one or more test to run. The plurality of tests can include, for example, a PCR analysis, a cytometry analysis and/or an enzyme-linked immunosorbent assay (ELISA) analysis. In an alternative embodiment, a plurality of different types of test cards 100 can be inserted into device 10, with each test card 100 corresponding to one or more specific test to be run on a fluid sample, and controller 28 can determine which test(s) to run by detecting the type of test card 100 inserted into device 10 without further instruction by the user. In another alternative embodiment, fluid microchannel 134 can be incorporated into device 10 rather than test card 100, and a user can choose a test to run on the fluid sample after the fluid sample is injected directly into device 10.

Input module 254 is configured to receive the user inputs inputted into user interface 60 and communicate the user inputs to control module 256. Input module 254 can also receive additional information via user interface 60 and/or by the preprogramming of controller 28, for example, (i)

real-time PCR crossover threshold value information; (ii) maximum fluorescence information; and (iii) melting curve inflection temperature information. Other control parameters for the PCR reaction can also be given. This includes the PCR denaturing, elongation and annealing temperatures and dwell times.

Once a test card 100 and/or fluid sample has been loaded into device 10, control module 256 of controller 28 begins the control method at step 200 by causing fluid actuation source 26 to pull fluid through microchannel 134. In the illustrated embodiment, fluid actuation source applies a negative pneumatic force to outlet port 130 via pneumatic tube 40 to pull fluid through microchannel 134. In an alternative embodiment, fluid actuation source can include one or more other type of pump in fluid communication with microchannel 134.

After fluid actuation source 26 has been activated, but before the reaction begins, control module 256 at step 202 can verify that fluid is located within target zone 166 by monitoring the capacitance of microchannel 134 at one or more locations upstream and/or downstream of target zone 166. If fluid is detected in microchannel 134 upstream and/or downstream of target zone 166, control module 256 can verify that fluid is located within target zone 166, activate light source 22 at step 204, and begin the reaction at step 206. Controller 28 can choose a portion of microchannel 134 to designate as target zone 166, or target zone 166 can be predetermined.

In the illustrated embodiment, control module 256 begins the reaction at step 206 by instructing power source 30 to send a current to electrodes located adjacent to target zone 166 via electrical contact device 26 to cause the fluid within target zone 166 to be heated. As the fluid sample is heated, the nucleic acid molecules multiply by diffusion as explained above.

At the same time that the fluid sample is being heated within target zone 166 so that the nucleic acid molecules multiply by diffusion, control module 256 at step 208 can cause camera imaging device 20 to record a plurality of images of the reaction within target zone 166. The plurality of images can then be sent to analysis module 208 for analysis at step 210. In an embodiment, test card 100 includes a transparent material that allows images to be taken of target zone 166 of fluid microchannel 134 even though a layer of polymer material is located between camera imaging device 20 and fluid microchannel 134.

At step 210, analysis module 258 analyzes the images taken by camera imaging device 20 to determine whether the fluid sample tests positive or negative for a bacteria or virus. The type of analysis performed by analysis module at step 210 will depend on the type of test being run on the fluid sample.

If the assay being run on the fluid sample is a PCR analysis, then analysis module 258 can analyze the images as discussed above by measuring fluorescence based on detected wanted and unwanted objects.

If the assay being run on the fluid sample is a cytometry analysis, then analysis module 258 can also analyze the images as discussed above by measuring fluorescence based on detected wanted and unwanted objects. The cytometry analysis can differ from the PCR analysis, for example, because the fluid in target zone 166 does not need to be heated to multiply molecules by diffusion, so step 206 can be skipped. With a cytometry analysis, analysis module 258 can analyze the fluid sample within target zone 166, for example, by analyzing cell size, cell count, cell morphology (shape and structure), cell cycle phase, DNA content, and the existence or absence of specific proteins on cell surfaces. In an embodiment, controller 28 can use various different fluorophores for flow cytometry. In an embodiment, to detect specific proteins on cell surfaces, specifically designed fluorophores which bind to those proteins are mixed into the sample to cause the proteins of interest to fluoresce.

If the assay being run on the fluid sample is an ELISA analysis, then again the fluid in target zone 166 does not need to be heated to multiply molecules by diffusion, so step 206 can be skipped. With an ELISA analysis, analysis module 258 can analyze the fluid sample within target zone 166, for example, by measuring the concentration of an analyte in the fluid sample using a colormetric analysis. In an embodiment, controller 28 can measure the amount of incident light scattered on the ELISA target zone to determine the concentration of an analyte. The method of measurement is the same as the turbidity measurement.

In an embodiment, controller 28 can perform genotyping tests as an extension a PCR.

At step 212, analysis module 258 determines based on the analysis whether the fluid sample has tested positive or negative for a bacteria or virus. The results of the analysis are then displayed on user interface 60 by output module 260. In an embodiment, a simple "POSITIVE" or "NEGATIVE" indication can be displayed on user interface 60 to inform whether the fluid sample has tested positive or negative for a bacteria or virus. In another embodiment, user interface 60 can display the results for more than one bacteria or virus, or can display specifics such as cell size, cell count, cell morphology (shape and structure), cell cycle phase, DNA content, and the existence or absence of specific proteins on cell surfaces. In an embodiment, controller 28 can display viral titer in the case of a PCR reaction, or can display protein concertation and DNA concentration.

In an embodiment, the result of the analysis can be saved in a memory module of memory 252, so that the results can be reviewed at a later time. If the result is saved, the result should be encoded to protect the anonymity of the patient. In another embodiment, one or more encoded results can be wirelessly transmitted for review at a location remote from diagnostic system 1.

In an embodiment, device 10 can include a global positioning system (GPS) sensor, and can record the result of the test along with a GPS sensor reading at the time of the test. Controller 28 can then aggregate a plurality of tests to determine viruses or bacteria that are more prevalent in one area as opposed to another. In this embodiment, controller 28 does not need to save any patient information, and only needs the GPS location and the number of positive and negative test results at the location to determine the prevalence of the virus or bacteria at the location. The results can be used by a health organization to treat an area with appropriate medication for a prevalent virus or bacteria.

In another embodiment, the user can program the location into device 10 before, during or after running a plurality of tests, and controller 28 can aggregate the plurality of tests to determine viruses or bacteria that are more or less prevalent in the programmed area.

In an embodiment, controller 28 can determine whether one or more of yersina *pestis, brucella*, alphavirus, dengue virus and/or variola virus is present in the fluid sample.

The diagnostic system 1 disclosed herein can detect, for example, lentiviruses (ssRNA) and adenoviruses (dsDNA) in whole blood, as well as other infectious agents. Exemplary infectious agents which can be detected by the system 1 disclosed herein include, but are not limited to, bacterial pathogens, viral pathogens, fungal pathogens, and/or parasitic pathogens.

Exemplary non-limiting bacterial pathogens include *Bacillus* (e.g., *Bacillus anthracis, Bacillus cereus*), *Bartonella* (e.g., *Bartonella henselae, Bartonella quintana*), *Bordatella* (e.g., *Bordatella pertussis*), *Borrelia* (e.g., *Borrelia burgdorferi, Borrelia garinii, Borrelia afzelii, Borrelia recurrentis*), *Brucella* (e.g., *Brucella abortus, Brucella canis, Brucella melitensis, Brucella suis*), *Campylobacter* (e.g., *Campylobacter jejuni*), *Chlamydia* (e.g., *Chlamydia pneumoniae, Chlamydia trachomatis*), *Chlamydophila* (e.g., *Chlamydophila psittaci*), *Clostridium* (e.g., *Clostridium botulinum, Clostridium difficile, Clostridium perfringens, Clostridium tetani*), *Corynebacterium* (e.g., *Corynebacterium diphtheriae*), *Enterococcus* (e.g., *Enterococcus faecalis, Enterococcus faecium*), *Escherichia* (e.g, *Escherichia coli*), *Francisella* (e.g., *Francisella tularensis*), *Haemophilus* (e.g., *Haemophilus influenzae*), *Helicobacter* (e.g., *Helicobacter pylori*), *Legionella* (e.g., *Legionella pneumophila*), *Leptospira* (e.g., *Leptospira interrogans, Leptospira santarosai, Leptospira weilii, Leptospira noguchii*), *Listeria* (e.g., *Listeria monocytogenes*), *Mycobacterium* (e.g., *Mycobacterium leprae, Mycobacterium tuberculosis, Mycobacterium ulcerans*), *Mycoplasma* (e.g., *Mycoplasma pneumoniae*), *Neisseria* (e.g., *Neisseria gonorrhoeae, Neisseria meningitidis*), *Pseudomonas* (e.g., *Pseudomonas aeruginosa*), *Rickettsia* (e.g., *Rickettsia rickettsii*), *Salmonella* (e.g., *Salmonella typhi, Salmonella typhimurium*), *Shigella* (e.g., *Shigella sonnei*), *Staphylococcus* (e.g., *Staphylococcus aureus, Staphylococcus epidermidis, Staphylococcus saprophyticus*), *Streptococcus* (e.g., *Streptococcus agalactiae, Streptococcus pneumoniae, Streptococcus pyogenes*), *Treponema* (e.g., *Treponema pallidum*), *Ureaplasma* (e.g., *Ureaplasma urealyticum*), *Vibrio* (e.g., *Vibrio cholerae*), and *Yersinia* (e.g., *Yersinia pestis, Yersinia enterocolitica, Yersinia pseudotuberculosis*).

Exemplary non-limiting viral pathogens include Adenoviridae (e.g., adenovirus), Herpesviridae (e.g., herpes simplex virus type 1 and type 2, varicella-zoster virus, cytomegalovirus, Epstein-Barr virus, human herpesvirus type 8), Papillomaviridae (e.g., human papillomavirus), Polyomaviridae (e.g., BK virus, JC virus), Poxviridae (e.g., smallpox), Hepadnaviridae (e.g., hepatitis B virus), Parvoviridae (e.g., human bocavirus, parvovirus B19), Astroviridae (e.g., human astrovirus), Caliciviridae, (e.g., Norwalk virus), Picornaviridae (e.g., Coxsackievirus, hepatitis A virus, poliovirus, rhinovirus); Coronaviridae (e.g., severe acute respiratory syndrome virus, Middle East respiratory syndrome virus), Flaviviridae (e.g., hepatitis C virus, yellow fever virus, dengue virus, West Nile virus), Togaviridae (e.g., rubella virus), Hepeviridae (e.g., hepatitis E virus), Retroviridae (e.g., lentiviruses, human immunodeficiency virus); Orthomyxoviridae (e.g., influenza virus), Arenaviridae (e.g., Guanarito virus, Junin virus, Lassa virus, Machupo virus, Sabiá virus), Bunyaviridae (e.g., Crimean-Congo hemorrhagic fever virus), Filoviridae (e.g., Ebola virus, Marburg virus), Paramyxoviridae (e.g., measles virus, mumps virus, parainfluenza virus, respiratory syncytial virus, human metapneumonia virus, Hendra virus, Nipah virus), Phabdoviridae (e.g., rabies virus), Reoviridae (e.g., rotavirus, orbivirus, coltivirus, Banna virus), and unassigned viruses (e.g., Hepatitis D virus).

Exemplary non-limiting fungal pathogens include *Candida* (e.g., *Candida albicans*), *Aspergillus* (e.g., *Aspergillus fumigatus, Aspergillus flavus*), *Crytopcoccus* (e.g., *Cryptococcus neoformans, Cryptococcus laurentii, Cryptococcus gattii*), *Histoplasma* (e.g., *Histoplasma capsulatum*), *Pneumocystis* (e.g., *Pneumocystis jirovecii, Pneumocystis carinii*), *Stachybotrys* (e.g., *Stachybotrys chartarum*).

Exemplary non-limiting parasitic pathogens include *acanthamoeba, anisakis, Ascaris lumbricoides*, botfly, *Balantidium coli*, bedbugs, *Cestoda* (tapeworm), chiggers, *Cochliomyia hominivorax, Entamoeba histolytica, Fasciola hepatica, Giardia lamblia*, hookworms, *Leishmania, Linguatula serrata*, liver flukes, *Loa loa, Paragonimus*—lung fluke, pinworm, *Plasmodium falciparum, Schistosoma, Strongyloides stercoralis*, mites, tapeworms, *Toxoplasma gondii, Trypanosoma*, whipworms, and *Wuchereria bancrofti*.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A device for analyzing a polymerase chain reaction in a fluid sample, the device comprising:
   a current source configured to cause the polymerase chain reaction by heating the fluid sample within a target zone;
   a camera imaging device configured to record a plurality of images of the fluid sample in the target zone while the current source causes the polymerase chain reaction; and
   a controller configured to (i) distinguish wanted objects in the plurality of images from an unwanted object in the plurality of images, and (ii) determine whether the fluid sample tests positive or negative for a bacteria or virus based on the wanted objects,
   wherein the wanted objects include at least one of nucleic acid molecules or cells, and the unwanted object includes an object that does not have at least one of an average size or an average shape of at least one of nucleic acid molecules or cells.

2. The device of claim 1, wherein the unwanted object is an air bubble, and
   wherein the controller is configured to detect the air bubble by identifying an object that expands in size during the polymerase chain reaction.

3. The device of claim 1, wherein the controller is configured to analyze the plurality of images by dividing the target zone into a plurality of bins.

4. The device of claim 3, wherein the plurality of bins are arranged in a grid with a plurality of rows and columns.

5. The device of claim 3, wherein the controller is configured to determine whether the fluid sample has tested positive or negative for the bacteria or virus by selecting at least two of the plurality of bins that overlap a cluster of wanted objects and calculating a mean fluorescence value of the at least two of the plurality of bins.

6. The device of claim 5, wherein the controller is configured to exclude at least one of the plurality of bins from the mean fluorescence value calculation if the at least one of the plurality of bins overlaps the unwanted object.

7. The device of claim 5, wherein the controller is configured to assign a weight to at least one of the plurality of bins used in the mean fluorescence value calculation based on the proximity of the at least one of the plurality of bins to the unwanted object.

8. The device of claim 5, wherein the controller is configured to exclude at least one of the plurality of bins if the at least one of the plurality of bins does not meet a minimum threshold value for brightness.

9. The device of claim 1, wherein the controller is configured to report an inconclusive test if the controller identifies at least one unwanted object in the plurality of images.

10. The device of claim 1, which includes a user interface, wherein the controller includes a plurality of preprogrammed analyses that can be performed on the fluid sample, and wherein the user interface is configured to allow a user to select at least one analysis from the plurality of preprogrammed analyses.

11. The device of claim 1, wherein the plurality of images includes at least one of: (i) a plurality of still images of the polymerase chain reaction recorded by the camera imaging device over a period of time; or (ii) a video image of the polymerase chain reaction recorded by the camera imaging device over the period of time.

12. The device of claim 1, wherein the controller is configured to distinguish the wanted objects in the plurality of images from the unwanted object in the plurality of images by comparing a size or shape of objects in the plurality of images to an average size or shape of blood cells.

13. A device for analyzing a polymerase chain reaction in a fluid sample, the device comprising:
   a current source configured to cause the polymerase chain reaction by heating the fluid sample within a target zone;
   a camera imaging device configured to record a plurality of images of the fluid sample in the target zone while the current source causes the polymerase chain reaction and a light source provides a fluorescence excitation light on the fluid sample; and
   a controller configured to analyze the plurality of images by (i) dividing the target zone shown in the plurality of images into a plurality of bins, (ii) selecting at least two of the plurality of bins, and (iii) calculating a fluorescence value of the selected at least two of the plurality of bins using fluorescence measurements included within the plurality of images.

14. The device of claim 13, wherein the controller is configured to select the at least two of the plurality of bins based on a threshold value for brightness.

15. The device of claim 13, wherein the controller is configured to exclude at least one of the plurality of bins from the fluorescence value calculation if the at least one of the plurality of bins overlaps an unwanted object,
wherein the unwanted object includes an object that expands in size during the polymerase chain reaction or an object that does not have at least one of an average size or an average shape of at least one of nucleic acid molecules or cells.

16. The device of claim 13, wherein the controller is configured to assign weights to the selected at least two of the plurality of bins for the calculation based on the proximity of the selected at least two of the plurality of bins to an unwanted object,
wherein the unwanted object includes an object that expands in size during the polymerase chain reaction or an object that does not have at least one of an average size or an average shape of at least one of nucleic acid molecules or cells.

17. A method of analyzing a polymerase chain reaction m a fluid sample comprising:
heating the fluid sample in a target zone to cause the polymerase chain reaction;
recording a plurality of images of the fluid sample in the target zone during the polymerase chain reaction while a light source provides a fluorescence excitation light on the fluid sample;
dividing the target zone into a plurality of bins;
calculating a fluorescence value of at least two of the plurality of bins using fluorescence measurements included within the plurality of images; and
determining whether the fluid sample tests positive or negative for a bacteria or virus based on the calculated fluorescence value.

18. The method of claim 17, wherein calculating the fluorescence value includes weighting the at least two of the plurality of bins based on proximity to an unwanted object.

19. The method of claim 17, wherein calculating the fluorescence value includes excluding at least one of the plurality of bins from the fluorescence value calculation if the at least one of the plurality of bins overlaps an unwanted object.

20. The method of claim 17, wherein calculating the fluorescence value includes excluding at least one of the plurality of bins based on a threshold value for brightness.

21. A device for analyzing a fluid sample, the device comprising:
a camera imaging device configured to record a plurality of images of the fluid sample that is undergoing a polymerase chain reaction while located within a target zone of a fluid microchannel; and
a controller configured to
compare a size or shape of objects in the plurality of images to an average size or shape of cells or nucleic acid molecules,
distinguish wanted objects in the plurality of images from an unwanted object in the plurality of images based on the wanted objects having the average size or shape of cells or nucleic acid molecules, and
determine whether the fluid sample tests positive or negative for a bacteria or virus based on the wanted objects.

22. The device of claim 21, wherein the controller is configured to determine whether the fluid sample tests positive or negative for the bacteria or virus by dividing the target zone shown in the plurality of images into a plurality of bins, selecting at least two of the plurality of bins, and calculating a fluorescence value of the selected at least two of the plurality of bins.

* * * * *